United States Patent [19]

Foulletier et al.

[11] 4,059,629

[45] Nov. 22, 1977

[54] PERFLUOROALIPHATIC SUBSTITUTED AMINE MIXTURES AND THE METHOD FOR PREPARING THE SAME

[75] Inventors: Louis Foulletier, Ouillins; Jean-Pierre Lalu, La Mulatiere, both of France

[73] Assignee: Produits Chimiques Ugine Kuhlmann, Paris, France

[21] Appl. No.: 593,173

[22] Filed: July 3, 1975

Related U.S. Application Data

[63] Continuation of Ser. No. 138,748, April 29, 1971, abandoned, which is a continuation-in-part of Ser. No. 819,481, April 25, 1969, abandoned, which is a continuation-in-part of Ser. No. 694,045, Dec. 28, 1967, abandoned.

[30] Foreign Application Priority Data

Dec. 29, 1972 France .............................. 70.30550

[51] Int. Cl.² .................. C07C 87/127; C07C 87/22; C07C 87/26; C07C 87/32
[52] U.S. Cl. ..................... 260/583 GG; 260/296 R; 260/326.85; 260/333; 260/563 R; 260/563 C
[58] Field of Search ..................... 260/583 GG, 583 H

[56] References Cited

U.S. PATENT DOCUMENTS

| | | | |
|---|---|---|---|
| 3,359,319 | 12/1967 | Fawcett | 260/583 GG |
| 3,535,381 | 10/1970 | Hauptschein et al. | 260/570.9 |

FOREIGN PATENT DOCUMENTS

| | | | |
|---|---|---|---|
| 1,532,284 | 7/1968 | France | 260/583 GG |
| A95,059 | 6/1970 | France | 260/583 GG |
| 1,594,924 | 5/1970 | Germany | 260/583 GG |

*Primary Examiner*—Daniel E. Wyman
*Assistant Examiner*—John J. Doll
*Attorney, Agent, or Firm*—Pennie & Edmonds

[57] ABSTRACT

The invention comprises perfluoroalkyl substituted amines of the formula $$C_nF_{2n+1}(CR^1R^2)_m-N-R^4 \quad (I)$$
$$\quad\quad\quad\quad\quad\quad\quad\quad\quad |$$
$$\quad\quad\quad\quad\quad\quad\quad\quad\quad R^3$$

wherein $n$ is an integer from 1 to about 20, $m$ is an integer between 2 or 4, $R^1$ and $R^2$ each is a hydrogen atom or a lower alkyl containing 1 to 3 carbon atoms and $R^3$ and $R^4$ each is a hydrogen atom, an alkyl containing 1 to 20 carbon atoms, an alkenyl containing 3 to 10 carbon atoms, a cycloparaffin radical containing 3 to 12 carbon atoms, a cycloalkenyl radical containing 5 to 12 carbon atoms, and N or O ring substituted cycloalkenyl radical containing 5 to 12 carbon atoms, or an aryl, or $R^3$ or $R^4$ are joined in the form of an alkylene radical of the formula $$-(CHR)_p-$$

wherein $p$ is an integer from 2 to 6 and R is a hydrogen atom or a lower alkyl containing 1 to 3 carbon atoms. These compounds are prepared by reacting at a temperature in the range between 0° to 200° C. perfluoroalkyl halides of the formula $$C_nF_{2n+1}(CR^1R^2)_mY \quad (II)$$

wherein $n$, $m$, $R^1$ and $R^2$ each has the same meaning as defined hereinabove and Y is an iodine or a bromine atom with amines of the formula

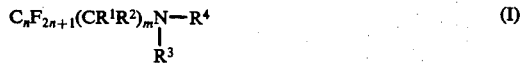

(III)

wherein $R^3$ and $R^4$ have the same meaning as previously stated.

The invention also comprises perfluoroalkyl substituted amines of the formula $$C_{n-1}F_{2n-1}-CF=CR^1-CHR^1-N-R^4 \quad (IV)$$
$$\quad\quad\quad\quad\quad\quad\quad\quad\quad\quad\quad\quad\quad\quad |$$
$$\quad\quad\quad\quad\quad\quad\quad\quad\quad\quad\quad\quad\quad\quad R^3$$

and mixtures of products of formula IV with $$C_nF_{2n+1}(CHR^1)_2-N-R^4 \quad (V)$$
$$\quad\quad\quad\quad\quad\quad\quad\quad\quad\quad |$$
$$\quad\quad\quad\quad\quad\quad\quad\quad\quad\quad R^3$$

in which $R^1$, $R^3$ and $R^4$ have the same meaning as designated above and where $n$ is an integer from 4 to 20.

The process for producing the products of formulas IV and V and mixtures thereof is the same as that used for the products of the compounds of formula I except that in the starting compounds of formula II at least one of the radicals $R^1$ or $R^2$ is hydrogen, $m$ is equal to 2 and $n$ is an integer between 4 and 20.

4 Claims, No Drawings

PERFLUOROALIPHATIC SUBSTITUTED AMINE MIXTURES AND THE METHOD FOR PREPARING THE SAME

CROSS REFERENCE TO RELATED APPLICATION

This application is a continuation of application Ser. No. 138,748 filed Apr. 29, 1971, now abandoned, which in turn is a continuation-in-part application of our prior application Ser. No. 819,481 filed Apr. 25, 1969, now abandoned, which in turn is a continuation-in-part of our earlier filed application Ser. No. 694,045, filed Dec. 28, 1967, now abandoned.

BACKGROUND OF THE INVENTION

I. Field of the Invention

This invention relates to mixtures of perfluoroaliphatic substituted amines and the method for preparing the same.

II. Description of the Prior Art

It is well known that nonfluorinated alkyl halides of the formula $$C_nH_{2n+1}X$$

wherein n is an integer and X is a halogen, react with ammonia and with amines to produce various substituted amine and quaternary ammonium slats. However, in the case of fluorinated alkyl halides of the formula:

$$C_nF_{2n+1}-CH_2CH_2-Y$$

wherein n and Y each has the same meaning as stated above, the halides become readily dehydrohalogenated in the presence of nucleophilic agents such as various amines which include the tertiary amine to yield fluorinated olefins of the formula $$C_nF_{2n+1}-CH=CH_2$$

SUMMARY OF THE INVENTION

We have discovered that it is possible according to the method of this invention to react perfluoroalkyl iodides or bromides with primary or secondary amines to produce perfluoroaliphatic substituted amines as the principal reaction product and a minor amount of a fluoro-olefin of the formula $$C_nF_{2n+1}-CH=CH_2$$

wherein n is an integer from 1 to about 20. Broadly stated, the perfluoroalkyl substituted amines of the invention have the formula $$C_nF_{2n+1}(CR^1R^2)_mN-R^4$$
$$\phantom{C_nF_{2n+1}(CR^1R^2)_mN-}|$$
$$\phantom{C_nF_{2n+1}(CR^1R^2)_mN-}R^3$$
(I)

wherein n as stated hereinabove is an integer from 1 to about 20, m is 2 or 4, $R^1$ and $R^2$ each is a hydrogen atom or a lower alkyl containing 1 to 3 carbon atoms, and $R^3$ and $R^4$ each is a hydrogen atom, an alkyl containing 1 to 20 carbon atoms, an alkenyl containing 3 to 10 carbon atoms, a cycloparaffin radical containing 3 to 12 carbon atoms, a cycloalkenyl radical containing 5 to 12 carbon atoms, an N or O ring substituted cycloalkenyl radical containing 5 to 12 carbon atoms or an aryl, or $R^3$ or $R^4$ are joined in the form of an alkylene radical of the formula $$-(CHR)_p-$$

wherein p is an integer form 2 to 6 and R is a hydrogen atom or a lower alkyl containing 1 to 3 carbon atoms.

The perfluoroaliphatic substituted amines of this invention are prepared by reacting at a temperature in the range between 0° and 200° C. a perfluoroalkyl halide of the formula $$C_nF_{2n+1}(CR^1R^2)_mY$$
(II)

wherein n, m, $R^1$ and $R^2$ each has the same meaning as defined hereinabove and Y is an iodine or a bromine atom with an amine of the formula

(III)

wherein $R^3$ and $R^4$ each also has the same meaning as previously stated.

When at least one of the radicals $R^1$ and $R^2$ is hydrogen, m is equal to 2 and n is an integer from 4 to 20, the reaction of compounds II and III simultaneously yields compounds of the formula $$C_nF_{2n+1}(CHR^1)_2-N-R^4$$
$$\phantom{C_nF_{2n+1}(CHR^1)_2-N-}|$$
$$\phantom{C_nF_{2n+1}(CHR^1)_2-N-}R^3$$
(V)

together with compounds of the formula $$C_{n-1}F_{2n-1}-CF=CR^1-CHR^1-N-R^4$$
$$\phantom{C_{n-1}F_{2n-1}-CF=CR^1-CHR^1-N-}|$$
$$\phantom{C_{n-1}F_{2n-1}-CF=CR^1-CHR^1-N-}R^3$$
(IV)

in which $R^1$, $R^3$ and $R^4$ have the same meaning as designated above and n is an integer of 4 to 20 which constitutes novel compounds and novel mixtures of the compounds of formulas IV and V.

DESCRIPTION OF THE PREFERRED EMBODIMENTS

Perfluoroalkyl halides of the formula $$C_nF_{2n+1}(CR^1R^2)_mY$$
(II)

when reacted with amines of the formula

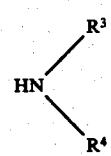
(III)

yield perfluoroalkyl amines of the formula $$C_nF_{2n+1}(CR^1R^2)_mN-R^4$$
$$\phantom{C_nF_{2n+1}(CR^1R^2)_mN-}|$$
$$\phantom{C_nF_{2n+1}(CR^1R^2)_mN-}R^3$$
(I)

The symbols n, m, $R^1$, $R^2$, $R^3$, $R^4$ and Y each has the same meaning as stated previously.

When the formula II compound of this process is selected to be a compound of the formula $$C_nF_{2n+1}(CHR^1)_2Y \qquad (VI)$$

in which n is an integer from 4 to 20 there is simultaneously produced a compound of the formula $$C_nF_{2n+1}(CHR^1)_2-\underset{\underset{R^3}{|}}{N}-R^4 \qquad (V)$$

together with a compound of the formula $$C_{n-1}F_{2n-1}-CF=CR^1-CHR^1-\underset{\underset{R^3}{|}}{N}-R^4 \qquad (IV)$$

The process of this invention may be carried out with or without the use of a solvent. The suitable solvents for the reaction preferably have boiling points below about 200° C. Examples of these solvents are as follows:

I. Halogenated hydrocarbons having from 1 to 4 carbon atoms; fluorinated, chlorinated, fluorochlorinated hydrocarbons preferably chloroform, carbon tetrachloride, methylene chloride, ethylene chloride, 1,1-dichlorethylene, difluorotetrachlorethane, trichlorotrifluoroethane;

II. Primary, secondary, or tertiary alcohol with 1 to 10 carbon atoms; n-butanol, isobutanol, n-pentanol, isopentanol, n-hexanol, 2-hexanol, 2-heptanol, n-heptanol, n-octanol;

III. Aliphatic cyclic, heterocyclic, or aromatic ethers; ethyl, propyl or isopropyl ethers, dioxane, tetrahydrofuran, tetrahydropyrane, anisole;

IV. Aliphatic, cyclic or aromatic ketones; 2-butanone, 2-pentanone, 3-pentanone, cyclohexanone, acetophenone;

V. Aliphatic or aromatic esters; propyl formate, methyl acetate, ethyl acetate, butyl acetate, phenyl acetate, methyl benzoate, ethyl benzoate;

VI. Tertiary amine; pyridine, 2-methylpyridine, N-methylpiperidine.

In addition, aprotic solvents can also be used. The suitable solvents of this type include dimethylformamide, dimethylsulfoxide, hexamethylophosphorotriamide. Among the various solvents mentioned, we prefer to use the tertiary amines.

As stated previously, the perfluoroalkyl halides of the following formula $$C_nF_{2n+1}(CR^1R^2)_mY$$

wherein n is an integer from 1 to about 20, m is 2 or 4, $R^1$, $R^2$ each is a hydrogen atom or lower alkyl containing 1 to 3 carbon atoms and Y is an iodine or a bromine atom, are suitable as starting material for preparing the perfluoroalkyl substituted amine or this invention. We, however, prefer to use iodides wherein n is in the range between 6 to 12, m is 2 and $R^1$ and $R^2$ each is hydrogen atom. The preferred iodides are prepared by reacting $C_nF_{2n+1}I$ with ethylene in the presence of a free radical generating initiator such as heat, α,α-azobisisobutyronitrile, benzoyl peroxide and the like; the reaction generates compounds containing an even number of methylene groups $-(CH_2)_m-$.

When the preferred iodides of formula VI are employed, the process of this invention will simultaneously produce a formula V compound admixed with a formula IV compound.

The suitable amines for the process of the invention are primary and secondary amines of the formula:

$$HN\begin{matrix}R^3\\R^4\end{matrix}$$

wherein $R^3$ and $R^4$ each is a hydrogen atom, an alkyl containing 1 to 20 carbon atoms, cycloparaffin radical containing 3 to 12 carbon atoms, or an aryl. The primary and secondary amines containing double bonds wherein $R^3$ and $R^4$ each is an alkenyl or a cycloalkenyl are also suitable for the process. In addition, we found $R^3$ and $R^4$ may be joined in the form of an alkylene radical of the formula $$-(CHR)_p-$$

wherein R is a hydrogen or a lower alkyl containing 1 to 3 carbon atoms and p is an integer from 2 to 6.

When $R^3$ and $R^4$ each is an alkyl, it typically may be a straight chain or a branched alkyl including methyl, ethyl n-propyl, i-propyl, n-butyl, t-butyl, i-butyl, n-pentyl, 2-pentyl, n-hexyl, n-heptyl, 3-heptyl, n-dodecyl and n-octadecyl. When $R^3$ and $R^4$ are joined together and is an alkenyl, it may be vinyl, allyl, propenyl, i-propenyl, 2-penten-2-yl, or ehepten-3-yl. When $R^3$ and $R^4$ are joined together and is a cycloparaffin radical, it may be cyclopropyl, cyclobutyl, cyclopentyl, cyclopenten-1-yl, cyclohexyl, cyclohexen-3-yl, 3-methylcyclohexen-3-yl, or 4-methylcyclohexen-3-yl. When $R^3$ and $R^4$ are joined together and is an aryl, it may be phenyl or naphtyl. The suitable cycloalkenyls include cycloalkenyls containing N or O in the ring such as 2-tetrahydrofuryl, 2-furyl, and 4-pyridyl.

The fluorinated compounds according to the invention have very interesting and varied applications. They can be used as synthesis intermediates, particularly as auxiliaries in the textile industry, for example, as hydrophobic, oleophobic, and anti-spotting agents and in preparation of dyestuffs. They have surface tension properties such that they can also be used as surface-active agents (surfactants). For example, $C_6F_{13}-C_2H_4-NH(C_4H_9)$ dissolved in water at a weight concentration of 0.017 percent, lowers the surface tension of the water to 35 dynes/cm at 32° C. The surface tension decreases more strongly the longer the fluorinated chain. The compound of formula IV and mixtures thereof with the compounds of formula V have the same utility as the saturated products of formula I as disclosed above.

Further to illustrate this invention specific examples are described hereinbelow. The following examples, 1-9, also produce mixtures of saturated and unsaturated perfluoroaliphatic amines as reported in examples 20-30. However, the corresponding unsaturated amines were not separated or recovered therefrom and therefore the yields reported for the saturated perfluoroaliphatic amines are in fact the yields of the mixture. Examples 31-34 did not yield a mixture of amines.

EXAMPLE 1

A mixture of $C_6F_{13}-C_2H_4I$ (47.4 grams, 0.1 mole) and n-butylamine (29.2 grams, 0.4 mole), dissolved in 100cm³ of amylalcohol, was heated with reflux and under continuous agitation at 113° C. for 8 hours. This mixture was then distilled from which there were obtained three fractions and a semi-solid residue.

a. 41° C/190 mm Hg. fraction: this fraction was washed with water, which yielded an aqueous phase at the top and a more dense organic phase. The organic phase, after drying over anhydrous sodium sulfate, weighed 6.5 grams; it was made up 98 percent of $C_6F_{13}$—CH=$CH_2$.

b. 55° C/190 mm Hg. fraction: this fraction, soluble in water, was essentially made up of n-butylamine.

c. 70° C/50 mm Hg. fraction: this fraction was made up of amyl alcohol.

d. Semi-solid residue: the residue was agitated with 80 cm$^3$ of a 10 weight-percent solution of NaOH. The resulting solution was then subjected to five successive extractions with 60 cm$^3$ of ethyl ether, and the other extracts were dried over anhydrous sodium sulfate. After evaporation of the ether, the liquid was distilled and there were obtained three fractions and a residue.

1. volatile products, 3.1 grams, containing: N-butylamine (55 percent), amyl alcohol (25 percent), $C_6F_{13}$—CH=$CH_2$(18 percent) and impurities (2 percent);

2. 56°–60° C/17 mm Hg. fraction, 6.3 grams, containing: amyl alcohol (80 percent) and $C_6F_{13}$—$C_2H_4$—NH($C_4H_9$) (20 percent);

3. 92° C/17 mm Hg. fraction, 24 grams, made up of $C_6F_{13}$—$C_2H_4$—NH($C_4H_9$);

4. solid residue, 2 grams, made up of the iodohydrate of $C_6F_{13}$—$C_2H_4$—NH($C_4H_9$).

The yields of the experiment were 55 percent with respect to $C_6F_{13}$—$C_2H_4$—NH($C_4H_9$), and 21 percent with respect to $C_6F_{13}$—CH=$CH_2$.

EXAMPLE 2

A mixture of $C_6F_{13}$—$C_2H_4$I (94.8 grams, 0.2 mole) and n-butylamine (58.4 grams, 0.8 mole) was heated with reflux (87°–91° C.) under continuous agitation for 3 hours. This mixture was then agitated with 100 cm$^3$ of a 15 percent aqueous solution of NaOH. The resulting solution was subjected to five successive extractions with 100 cm$^3$ of ethyl ether, and the ether extracts were dried over anhydrous sodium sulfate. After evaporation of the ether, the liquid was distilled and there were obtained two fractions and a residue.

a. 40° C/100 mm Hg. fraction: this fraction was washed with water, which gave an aqueous phase at the top and a more dense organic phase. The organic phase, after drying over anhydrous sodium sulfate, weighed 27 grams; it was made up of $C_6F_{13}$—CH=$CH_2$ (45 percent), and of $C_6F_{13}$—$C_2H_4$—NH($C_4H_9$) (55 percent);

b. 100° C/20 mm Hg. fraction: 41 grams of $C_6F_{13}$—$C_2H_4$—NH($C_4H_9$);

c. Residue: 2 grams, made up of the iodohydrate of $C_6F_{13}$—$C_2H_4$—NH($C_4H_9$).

The yields of the experiment were 69 percent for $C_6F_{13}$—$C_2H_4$—NH($C_4H_9$) and 17 percent for $C_6F_{13}$—CH=$CH_2$.

EXAMPLE 3

A mixture of $C_6F_{13}$—$C_2H_4$I (47.4 grams, 0.1 mole) and n-butylamine 29.2 grams, (0.4 mole), dissolved in pyridine (100 cm$^3$), was heated with reflux at 100°–108° C. for 4 hours and 30 minutes under continuous agitation. This mixture was then distilled and there were obtained two fractions and a residue.

a. 50° C/100 mm Hg. fraction: this fraction was washed in water, which gave an aqueous phase at the top and a more dense organic phase. The organic phase, after drying over anhydrous sodium sulfate, weighed 3.1 grams, and was made up of $C_6F_{13}$—CH=$CH_2$ (43 percent) and $C_6F_{13}$—$C_2H_4$—NH($C_4H_9$) (57 percent).

b. 52° C/100 mm Hg. fraction: this fraction was made up of pyridine.

c. Residue: the residue was agitated with a 10 percent by weight NaOH solution. The resulting solution was extracted with ethyl ether, and then the ether extracts were dried over anhydrous sodium sulfate. After evaporation of the ether, the liquid was distilled and there were obtained two fractions and a residue.

1. volatile products: 15.6 grams, made up of n-butylamine and pyridine;

2. 93° C/17 mm Hg. fraction: 29.7 grams of $C_6F_{13}$—$C_2H_4$—NH($C_4H_9$);

3. residue: 2 grams, made up of the iodohydrate of $C_6F_{13}$—$C_2H_4$—NH($C_4H_9$);

The yields in the experiment were 80 percent of $C_6F_{13}$—$C_2H_4$—NH($C_4H_9$) and 4 percent for $C_6F_{13}$—CH=$CH_2$.

Table A sums up the results obtained in the reactions $C_6F_{13}$—$C_2H_4$I/ n-butylamine in various solvents.

EXAMPLE 4

A mixture of $C_4F_9$—$C_2H_4$—I (74.8 grams, 0.2 mole) and diethylamine (58 grams, 0.8 mole), dissolved in 200 cm$^3$ of pyridine, was heated with reflux and under continuous agitation at 70°–81° C. for 4 hours. The mixture was then agitated with 15 percent by weight aqueous solution of NaOH. There were thus obtained two phases: one organic; the other aqueous. The latter was extracted with ethyl ether (five) successive extractions with 50 cm$^3$), and the other extracts were combined with the organic phase. The ether was evaporated and then the residual liquid was distilled. There were thus obtained three fractions.

a. 45°–75° C/250 mm Hg. fraction: this fraction was washed with water and two phases were recovered. The most dense phase, after drying over anhydrous sodium sulfate, weighed 10.3 grams; it was made up of $C_4F_9$—$C_2H_4$—N($C_2H_5$)$_2$(88 percent), $C_4F_9$—CH=$CH_2$ (6 percent), and pyridine (6 percent).

b. 50° C/70 mm Hg.: subjecting this fraction to the same treatment as the preceding one, there were isolated 11.9 grams containing $C_4F_9$—$C_2H_4$—N($C_2H_5$)$_2$ (78 percent), $C_4F_9$—CH=$CH_2$ (18 percent), and pyridine (4 percent).

c. 60° C/15 mm Hg. fraction: 27.2 grams; this fraction was made up of $C_4F_9$—$C_2H_4$—N($C_2H_5$)$_2$ (95 percent pyridine (3 percent), and an unidentified constituent (2 percent).

The yields from the experiment rose to 70 percent for $C_4F_9$—$C_2H_4$—N($C_2H_5$)$_2$ and to 5.7 percent for $C_4F_9$—CH=$CH_2$.

Table A

| $C_6F_{13}$-$C_2H_4$I | | $C_4H_9NH_2$ | | Solvent in | Duration of | $C_6H_{13}$-$C_2H_4$-NH-($C_4H_9$) | |
| --- | --- | --- | --- | --- | --- | --- | --- |
| gm. | mole | gm. | mole | cm$^3$ | the Experiment hours | gm. | %yield |
| 47.4 | 0.1 | 29.2 | 0.4 | ethyl alcohol 100 | 8 | 16 | 39 |

Table A-continued

| $C_6F_{13}$-$C_2H_4I$ | | $C_4H_9NH_2$ | | Solvent in | Duration of the Experiment | $C_6H_{13}$-$C_2H_4$-NH-$(C_4H_9)$ | |
|---|---|---|---|---|---|---|---|
| gm. | mole | gm. | mole | cm$^3$ | hours | gm. | %yield |
| 23.7 | 0.05 | 14.6 | 0.2 | chloroform 25 | 10 | 13 | 62 |
| 47.4 | 0.1 | 29.2 | 0.4 | any alcohol 100 | 8 | 27.5 | 65 |
| 94.8 | 0.2 | 58.4 | 0.8 | — | 3 | 57.7 | 69 |
| 47.4 | 0.1 | 29.2 | 0.4 | Pyridine 100 | 4.5 | 33.5 | 80 |

Note:
All the reactions were carried out with reflux.

EXAMPLE 5

A mixture of $C_4F_9$—$C_2H_4$—I, 33.4 grams; 0.089 mole) and allylamine (20.3 grams; 0.36 mole) dissolved in 90 cm$^3$ of pyridine were heated with reflux and under continuous agitation at 78°-86° C. for 4 hours. The mixture was distilled and there were obtained three fractions and a residue:

a. 44°-48° C/760 mm Hg. fraction: 6.8 grams: this fraction was made up of $C_4F_9$—CH=$CH_2$ (63 percent) and of $C_4F_9$—$C_2H_4$—NH($CH_2$—CH=$CH_2$) (37 percent);

b. 48°-58° C/760 mm Hg. fraction: 6.7 grams: this fraction was made up of $CH_2$=CH—$CH_2$—$NH_2$ (75 percent) and $C_4F_9$—$C_2H_4$—NH($CH_2$—CH=$CH_2$) (24 percent);

c. 55° C/100 mm Hg. fraction: this fraction was made up of pyridine.

d. Residue: the residue was agitated with 60 cm$^3$ of a 15 percent by weight aqueous solution of NaOH. The resulting solution was extracted five times with 50 cm$^3$ of ethyl ether, and the ether extracts were then dried over anhydrous sodium sulfate. After evaporation of the ether, the liquid was distilled and there were obtained two fractions and a residue:

1. 45°-85° C/50 mm Hg. fraction: 2.3 grams: this fraction was made up of $C_4F_9$—$C_2H_4$—NH(CH$_2$—CH=$CH_2$) (63 percent) and unidentified constituent (37 percent);

2. 85° C/50 mm Hg.: 7.2 grams: this fraction contained $C_4F_9$—$C_2H_4$—NH($CH_2$—CH=$CH_2$) up to 99 percent;

3. Residue: 1 gram: this solid is the iodohydrate of $C_4F_9$—$C_2H_4$—NH($CH_2$—CH=$CH_2$).

The yields were 60 percent for $C_4F_9$—$C_2H_4$—NH($CH_2$—CH=$CH_2$) and 19 percent for $C_4F_9$—CH=$CH_2$.

EXAMPLE 6

A mixture of $C_6F_{13}$—$C_2H_4$—I (47.6 grams; 0.1 mole) allylamine (22.8 grams; 0.4 mole) dissolved in 100 cm$^3$ of pyridine was heated with reflux and under continuous agitation at 91°-98° C. for 4 hours. The mixture was distilled and there were obtained three fractions and a residue:

a. 38° C/400 mm Hg. fraction: 12.8 grams: this fraction was washed with water which gave an aqueous phase at the top and a denser organic phase. The latter, after drying over anhydrous sodium sulfate, weighed 5.3 grams and was made up of $C_6F_{13}$—CH=$CH_2$;

b. 38°-90° C/400 mm Hg. fraction: the two phases which made up this fraction were decanted. The lighter was pyridine, and the denser (6.7 grams) was $C_6F_{13}$—CH=$CH_2$, in the amount of 99.4 percent;

c. 55° C/100 mm Hg. fraction: this fraction was made up of pyridine;

d. Residue: the residue was agitated with 60 cm$^3$ of a 15 percent by weight aqueous solution of NaOH. The resulting solution was extracted five times with 50 cm$^3$ of ethyl ether, and the ether extracts were then dried over anhydrous sodium sulfate. After evaporation of the ether, the liquid was distilled and there were obtained two fractions and a residue:

1. 38° C/60 mm Hg. fraction: this fraction was made up of pyridine in the amount of 98 percent;

2. 70° C/5 mm Hg. fraction: this fraction was made up of $C_6F_{13}$—$C_2H_4$—NH($CH_2$—CH=$CH_2$) in the amount of 99 percent;

3. Residue: 1 gram: this solid is the iodohydrate of $C_6F_{13}$—$C_2H_4$—NH($CH_2$—CH=$CH_2$).

The yields were 56 percent for $C_6F_{13}$—$C_2H_4$—NH($CH_2$—CH=$CH_2$) and 32 percent for $C_6F_{13}$—CH=$CH_2$.

EXAMPLE 7

$C_6F_{13}$—$C_2H_4$—I (94.8 grams; 0.2 mole), methylamine (24.8 grams: 0.8 mole) and pyridine (200 cm$^3$) were introduced into a stainless steel autoclave with a capacity of 800 cm$^3$. The autoclave was cooled in liquid nitrogen and was evacuated to eliminate the inerts. The mixture was heated at 100° C. for 4 hours, and it was noted that the pressure went from 2.5 bars to 1.5 bars in the course of the operation. The autoclave was cooled and its contens were agitated with a 15 percent by weight aqueous solution of NaOH (80 cm$^3$). The solution was extracted with ethyl ether (4 times, 100 cm$^3$) and the ether extracts were dried over anhydrous sodium sulfate. After filtration of the latter, the ether was evaporated and the residual liquid distilled. There were thus obtained three fractions:

a. 38° C/80 mm Hg. fraction: to this fraction there were added 25 cm$^3$ of water, which led to the decantation of a dense phase which is made up of $C_6F_{13}$—CH=$CH_2$ (87 percent) and of $C_6F_{13}$—$C_2H_4$—NH($CH_3$) (12 percent);

b. 67° C/14 mm Hg. fraction: 48.2 grams: this fraction is made up of $C_6F_{13}$—$C_2H_4$—I (5 percent) and $C_6F_{13}$—$C_2H_4$—NH($CH_3$) (95 percent);

c. Residue: 2.1 grams: this solid residue is the iodohydrate of $C_6F_{13}$—$C_2H_4$—NH($CH_3$).

The yields in the experiment were 66 percent for $C_6F_{13}$—$C_2H_4$—NH($CH_3$), 26 percent for $C_6F_{13}$—CH=$CH_2$ and $C_6F_{13}$—$C_2H_4$—I was recovered in the amount of 2.5 percent.

EXAMPLE 8

A mixture of $C_4F_9$—$C_2H_4$—I (37.4 grams; 0.1 mole) and aniline (52 grams; 0.56 mole) was held between 120 and 150° C. for 4 hours, with continuous agitation. The mixture was then agitated with 100 cm³ of a 10 percent by weight aqueous solution of NaOh. The resulting solution was subjected to five successive extractions with ethyl ether (50 cm³) and the ether extracts were then dried over anhydrous sodium sulfate. After evaporation of the ether, the liquid was distilled and there were obtained three fractions and a residue:

a. 42°-95°/50 mm fraction: 4.2 grams: made up of $C_4F_9—CH=CH_2$, 7.3 percent; $C_6H_5—NH_2$, 87.2 percent; $C_4F_9—CH_2CH_2—I$ 3.3 percent; $C_4F_9—CH_2CH_2—NH(C_6H_5)$, 2.1 percent;

b. 100°/50 mm fraction: 38 grams: made up of $C_6H_5—NH_2$, 93.2 percent and of $C_4F_9—C_2H_4—NH(C_6H_5)$, 6.7 percent;

c. 125°/8-10 mm fraction: 25 grams: made up of $C_6H_5—NH_2$, 1 percent, and of $C_4F_9—C_2H_4—NH(C_6H_5)$, 99 percent;

d. Residue: 1 gram: unidentified solid.

The yield in the experiment was 91 percent with respect to

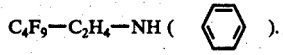

EXAMPLE 9

A mixture of $C_4F_9—C_2H_4—I$ (37.4 grams; 0.1 mole) and cyclohexylamine (39.4 grams; 0.4), dissolved in pyridine (100 cm³), was held between 85 and 120° C. for five hours, under constant agitation. The mixture was then agitated with 80 cm³ of a 10 percent by weight aqueous solution of NaOH. This treatment led to decantation of two phases; one dense organic phase, and the other aqueous. The aqueous phase was subjected to five successive extractions with ethyl ether (50 cm³), and then the ether extracts were dried over anhydrous sodium sulfate, before being added to the organic phase obtained by decantation. The ether was evaporated from the mixture, the liquid was distilled, and there were thus obtained four fractions and a residue:

a. 80°/400 mm, 56.5 grams, made up of $C_4F_9—CH=CH_2$, 4 percent; $C_5H_5N$, 70.8 percent; $C_6H_{11}-NH_2$, 23.4 percent; and

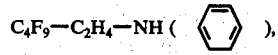

1.2 percent;

b. 110°/400 mm fraction: 20 grams, made up of $C_5N_5N$, 20.4 percent; $C_6H_{11}$, 77 percent and $C_4F_9—CH_2CH_2—NH(C_6H_{11})$, 2.6 percent;

c. 45°-100°/20 mm fraction: 7.3 grams, made up of $C_5H_5N$, 11 percent; $C_6H_{11}—NH_2$, 50.6 percent and $C_4F_9—C_2H_4—NH(C_6H_{11})$, 38.4 percent;

d. 100°-105°/20 mm fraction: 13.2 grams, made up of $C_5H_5N$, 3.7 percent; $C_6H_{11}—NH_2$, 5.3 percent and $C_4F_9—C_2H_4—NH(C_6H_{11})$, 91 percent;

e. Residue, 3 grams, unidentified solid.

The yield in the experiment was 65 percent with respect to $C_4F_9—C_2H_4—NH(C_6H_{11})$.

EXAMPLE 10

$C_4F_9—C_2H_4—I$ (37.4 grams; 0.1 mole) was added to a solution of pyrrolidine (25.2 grams; 0.4 mole) in pyridine (100 cm³). In the course of the addition, it was noted that an exothermic reaction raised the temperature of the reaction medium from 20° to 60°. The mixture was then heated to 110° C. during 4 hours, under continuous agitation. At the end of the reaction, the mixture was distilled and there were obtained four fractions and a residue:

a. 52°-78°/300 mm fraction: 5.6 grams, this fraction is miscible in water;

b. 55°/100 mm fraction: 95 grams, made up of pyrrolidine (3 percent), pyridine (94.8 percent), and

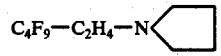

(2.1 percent);

c. 35°/10 mm fraction: 12.7 grams, made up of pyridine (89 percent), pyrrolidine (1.5 percent), and

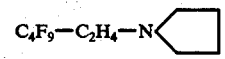

d. 58°/10 mm: 17.2 grams, made up of pyridine (1.4 percent, two unidentified compounds (0.6 percent), and

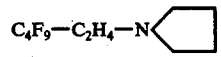

e. Liquid-solid residue; 7 grams; residue not analyzed.

The yield of the experiment was 89 percent with respect to $C_4F_9—C_2H_4—N$.

EXAMPLE 11

Into a stainless-steel autoclave with a capacity of 800 cc, $C_6F_{13}—C_2H_4—I$ (94.8 g; 0.2 mole), ammonia (31 g; 1.82 mole), and amyl alcohol (200 cc) were introduced. The autoclave was cooled in liquid nitrogen and placed under vacuum to eliminate inert gases. The autocalve was allowed to warm up to room temperature, the stirring equipment was started, and the autoclave was brought to 80° in 30 minutes and kept at this temperature for 3 hours 30 minutes. After cooling, a liquid was recovered and submitted to distillation. Two fractions and a residue were thus obtained:

a. Fraction 42°/100 mm Hg.: This fraction is made up of two phases. The denser phase (27.8 g) is made up of $C_6F_{13}—CH=CH_2$ (0.08 mole);

b. Fraction 85°/100 mm Hg.: was made up of amyl alcohol;

c. Residue.

This yield was stirred with a 10 percent by weight aqueous solution of NaOH. The resulting solution was extracted with ethyl ether (4 times 100 cc), and the etheral extracts were dried over anhydrous sodium sulfate. After evaporation of the ether, the residual liquid was distilled, and two fractions were obtained:

a. Fraction 30°-90°/100 mm Hg.: 2.6 g, made up of amyl alcohol (40 percent) and of $C_6F_{13}—C_2H_4—NH_2$ (60 percent; 0.0061 mole);

b. Fraction 94°-96°/100 mm Hg.: 29.1 g, made up of $C_6F_{13}—C_2H_4—NH_2$ (99 g; 0.08 mole), and of $C_6F_{13}—C_2H_4—I$ (1 percent).

The rate of conversion for $C_6F_{13}-C_2H_4-NH_2$ is 43 percent.

EXAMPLE 12

Into a stainless steel autoclave, 800 cc of $C_8F_{17}—_2H_4—I$ (202 g; 0.35 mole), methylamine (43.4 g; 1.4 mole)

dissolved in pyridine (350 cc) were introduced. The autoclave was cooled in a liquid nitrogen bath, and the inert gases eliminated by suction under vacuum. The autoclave was allowed to warm up to room temperature, the stirring device was started, and the apparatus brought to a temperature of 70° within 30 minutes which was maintained during 4 hours. After cooling, a liquid made up of two phases was recovered. The denser phase was stirred with 50 cc of a 10 percent-by-weight aqueous solution of NaOH., then washed with 100 cc of water, and, after drying over anhydrous sodium sulfate, was distilled. Two fractions and a residue were thus obtained:

a. Fraction 58°–76°/200 mm Hg. This fraction was washed with 50 cc of water, and this brought about the decantation of a denser phase (47.6 g) made up of $C_8F_{17}$—CH=$CH_2$ (88 percent; 0.093 mole), of $C_8F_{17}$—$C_2H_4$—I (4 percent; 0.0042 mole), and of $C_8F_{17}$—$C_2H_4$—NH-$CH_3$ (7 percent; 0.008 mole);

b. Fraction 93/20 mm Hg.: 96.1 g made up of $C_8F_{17}$—$C_2H_4$NH-$CH_3$ (0.202 mole).

c. Solid residue: 2 g: solid not identified.

The rate of conversion for $C_8F_{17}$—$C_2H_4$—NH—$CH_3$ is 60 percent.

EXAMPLE 13

Into a stainless steel autoclave, 800 cc of $C_{10}F_{21}$—$C_2H_4$—I (67.4 g; 0.1 mole), methylamine (12.4 g; 0.4 mole) dissolved in pyridine (100 cc) were introduced. The autoclave was cooled in a liquid nitrogen bath, and the inert gases eliminated by suction under vacuum. The autoclave was allowed to warm up to room temperature, then the stirring device was started, the apparatus brought to a temperature of 80° within 30 minutes, and kept at this temperature during 3 hours 30 minutes. After cooling, a liquid consisting of two phases was recovered; a light phase (A) and a dense phase (B). Phase (A) was stirred with 50 cc of a 10 percent aqueous soluton of NaOH, and this brought about the decantation of a phase (C) which was added to phase (B). Phases (B) and (C) were united, and then extracted with ethyl ether (4 times 100 cc). The etheral extracts were dried over anhydrous sodium sulfate and then distilled. Besides ethyl ether, four fractions were obtained:

a. Fraction 48°–58°/100 Hg. was made up of two phases. The upper, lighter phase is made up of pyridine; the denser phase (2.7 g) is made up of pyridine (3.5 percent), of $C_{10}F_{21}$—CH=$CH_2$ (70.9 percent); 0.0036 mole, and of $C_{10}F_{21}$—$C_2H_4$—NH—$CH_3$ (25.6 percent; 0.0013 mole);

b. Fraction 58°/100 mm Hg. was made up of pyridine;

c. Fraction 30°–116°/20 mm Hg. 2.6 g. was made up of $C_{10}F_{21}$—CH=$CH_2$ (40 percent; 0.0018 mole) and of $C_{10}F_{21}$—$C_2H_4$—NH—$CH_3$ (60 percent; 0.0028 mole);

d. Fraction 116°–118°/20 mm Hg. 44 g was made up of $C_{10}F_{21}$—$C_2H_4$—NH—$CH_3$ (0.071 mole).

The rate of conversion is 75 percent.

EXAMPLE 14

A mixture of $C_8F_{17}$—$C_2H_4$—I (144.5 g; 0.25 mole), normal-butylamine (73 g; 1 mole), and pyridine (250 cc) were heated at 100° during 4 hours, under constant stirring. After decantation of the reaction medium, which was made up of two phases, one light A, the other dense B, 150 cc of water was added to the light phase A, and this brought about the decantation of a dense phase which was added to the phase B. The two phases together were then stirred with a 10 percent-by-weight aqueous solution of NaOH (250 cc), then washed with water, and finally the organic phase was dried over anhydrous sodium sulfate. Three fractions and a residue were then recovered by distillation:

a. Fraction 30°/10 mm Hg.: This fraction was washed with water, and this brought about the decantation of 11.2 g of $C_8F_{17}$—CH=$CH_2$ (0.25 mole);

b. Fraction 45°/10 mm Hg.: 8.3 g was made up of $C_8F_{17}$—CH=$CH_2$ (97 percent; 0.018 mole), $C_8F_{17}$—$C_2H_4$—I (1.8 percent), and of $C_8F_{17}$—$C_2H_4$—NH-n$C_4H_9$ (1.2 percent);

c. Fraction 90°/2-3 mm Hg.: 93.2 g; $C_8F_{17}$—$C_2H_4$—NH—n$C_4H_9$ (0.18 mole);

d. Residue: 2.2 g. Solid not identified.

The conversion rate for $C_8F_{17}$—$C_2H_4$—NH—n$C_4H_9$ is 72 percent.

EXAMPLE 15

A mixture of $C_8F_{17}$—$C_2H_4$—I (57.4 g; 0.1 mole), diethylamine (29.2 g; 0.4 mole), and pyridine (100 cc) was heated at 80° during 4 hours under constant stirring. A light phase (A) and a dense phase (B) were thus obtained. Phase (A) was stirred with 50 cc of a 10 percent aqueous solution of NaOH, and this brought about the decantation of a phase (C) which was added to phase (B). Phases (B) and (C) thus united were stirred with 50 cc of a 5 percent aqueous solution of NaOH, then washed with 50 cc of water, extracted with ethyl ether (4 times 50 cc), dried over anhydrous sodium sulfate, and finally distilled. Two fractions were thus obtained:

a. Fraction 43°–84°/10 mm Hg.: 21.5 g was made up of $C_8F_{17}$—CH=$CH_2$ (92 percent; 0.044 mole), of $C_8F_{17}$—$C_2H_4$—I (1 percent), and of $C_8F_{17}$—$C_2H_4$—N$(C_2H_5)_2$ (7 percent; 0.0033 mole);

. Fraction 84°/5 mm Hg.: 25.2 g was made up of $C_8F_{17}$—$C_2H_4$—N$(C_2H_5)_2$ (0.0486 mole).

The conversion rates for $C_8F_{17}$—$C_2H_4$—$(C_2H_5)_2$ and for $C_8F_{17}$—CH=$CH_2$ are 52 percent and 44 percent respectively.

EXAMPLE 16

A mixture of $C_6F_{13}$—$C_2H_4$—I (23.7 g; 0.05 mole) and of N-methylaniline (19 g; 0.2 mole) was heated at 100° during 3 hours, under constant stirring. The mixture was then stirred with 50 cc of a 10 percent aqueous solution of NaOH, and the resulting solution extracted with ethyl ether (4 times 50 cc). The etheral extracts were dried over anhydrous sodium sulfate and then distilled. Besides the ether, three fractions were thus obtained:

a. Fraction 93°/50 mm Hg.: 8.9 g was made up of $C_6F_{13}$—$C_2H_4$—I (74.3 percent; 0.0175 mole) and of N-methylaniline (25.7 percent; 0.0006 mole);

b. Fraction 78°/10 mm Hg.: 9 g was made up of $C_6F_{13}$—$C_2H_4$—I (1 percent), of N-methylaniline (93 percent), and of

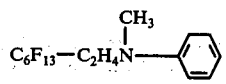

(6 percent; 0.0032 mole);

c. Fraction 116°/2-3 mm Hg.: 8.9 g was made up of N-methylaniline (4.8 percent) and of

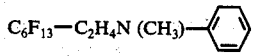

(95.2 percent; 0.0194 mole).

The conversion rates and yields of

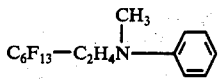

are 47 percent and 72.5 percent respectively.

EXAMPLE 17

$C_6F_{13}$—$C_2H_4$—I (94.8 g; 0.2 mole) was added under constant stirring to a solution of pyrrolidine (50.4 g; 0.8 mole) in pyridine (200 cc). The temperature of the mixture went from 20° to 65°. The reaction medium was then brought to 100°, and kept at this temperature during 4 hours with the help of an oil bath. After this period, the reaction medium was made up of two phases which were separated by decantation. An upper, lighter layer (A) and a dense phase (B) were thus collected. Phase (A) was stirred with 100 cc of a 10 percent aqueous solution of NaOH, and this brought about the decantation of a phase (C), which was added to phase (B). Phases (B) and (C) thus united were stirred with 50 cc of a 5 percent aqueous solution of NaOH, then washed with 50 cc of water, extracted with ethyl ether (4 times 50 cc), dried over anhydrous sodium sulfate, and finally distilled. Two fractions were thus obtained:

a. Fraction 36°-95°/20 mm Hg.: 3.1 g, was made up of $C_6F_{13}$—CH=$CH_2$ (0.6 percent), $C_6F_{13}$—$C_2H_4$—I (22 percent; 0.0017 mole), and $C_6F_{13}$—$C_2H_4N$—$C_4H_9$ (74 percent; 0.0057 mole);

b. Fraction 97°-100°/20 mm Hg.: 68.8 g made up of $C_6F_{13}$—$C_2H_4$—N—$C_4H_9$ (0.165 mole).

The conversion rate for $C_6F_{13}$—$C_2H_4N$—$C_4H_9$ is 85 percent.

EXAMPLE 18

A mixture of $C_8F_{17}$—$C_2H_4$—I (57.4 g; 0.1 mole), of N-methylcyclohexylamine (45.2 g; 0.4 mole), and of pyridine (100 cc) was heated at 80° during 4 hours, under constant stirring. After completion of the reaction, the reaction medium was made up of two phases: a light one (A), the other dense (B), which were separated by decantation. The upper, light phase (A) was stirred with 50 cc of a 10 percent aqueous solution of NaOH, and this brought about the decantation of a phase (C) which was added to phase (B). The phase (B) and (C) thus united were stirred with 50 cc of a 5 percent aqueous solution of NaOH, then washed with 50 cc of water extracted with ethyl ethyl ether (4 times 50 cc), dried over anhydrous sodium sulfate, and finally distilled. Three fractions and a residue were thus obtained:

a. Fraction 56°/20 mm Hg.: 14 g was made up of $C_6F_{13}$—$C_2H_4$—I (98.5 percent; 0.112 mole) and of

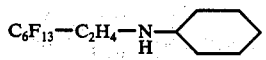

(1.4 percent; 0.0018 mole);

b. Fraction 128°/20 mm Hg.: 26.9 g was made up of

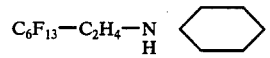

(0.0605 mole).

The conversion rate and yield of

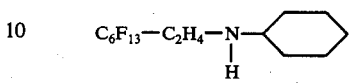

were 31 percent and 71 percent respectively.

EXAMPLE 20

A mixture of $C_6F_{13}$—$C_2H_4$—I (94.8 g; 0.2 mole) and methyl amine (24.8 g) was dissolved in 200 $cm^3$ pyridine in an 800 $cm^3$ autoclave. The autoclave was cooled with liquid nitrogen and placed under vacuum to remove inert gases. The autoclave was then heated at 100° C for 4 hours during which period it was observed that the pressure within the flask passed from 2.5 bars to 1.5 bars. After cooling, 80 $cm^3$ of a 15 percent aqueous solution of NaOh was added with agitation to the solution which was then extracted four times with 100 $cm^3$ of ethyl ether and the ether extracts were dried over anhydrous sodium sulfate. After filtration, the ether was evaporated and the liquid distilled. There were thus obtained two fractions and a residue:

a. 38° C/80 mm Hg. fraction: This fraction was combined with 25 $cm^3$ of water and there remained after decantation, a dense organic phase, 19.3 g was made up of $C_6F_{13}$ —CH=$CH_2$ (87 percent), $C_6F_{13}$—$C_2H_4$—N-H—$CH_3$ (1.2 percent) and $C_5F_{11}$=CH—$CH_2$—N-H—$CH_3$ (11 percent).

b. 67° C/18 mm Hg. fraction: 46.2 g containing $C_6F_{13}$—$C_2H_4$—I (5 percent, $C_6F_{13}$—$C_2H_4$—NH—$CH_3$ (13.3 percent) and $C_5F_{11}$—CF=CH—$CH_2$—NH—$CH_3$ (11 percent).

c. Residue: 2/1 g essentially the iodohydrate of $C_6F_{13}$ —$C_2H_4$—NH—$CH_3$.

The yields of the experiment were 57 percent for $C_5F_{11}$—CF=CH—$CH_2$—NH—$CH_3$, 9.2 percent for $C_6F_{13}$ —$C_2H_4$—NH—$CH_3$, 26 percent for $C_6F_{13}$ —CH=$CH_2$ and 2.5 percent for $C_6F_{13}$ —$C_2H_4$—I.

EXAMPLE 21

A mixture of $C_8F_{17}$—$C_2H_4$—I (202 g) and methyl amine (43.4 g), dissolved in 350 $cm^3$ of pyridine in an 800 $cm^3$ autoclave. The autoclave was cooled with liquid nitrogen and placed under vacuum to remove inert gases. The autoclave was permitted to warm up to ambient temperature, agitation was started and within 30 minutes, the temperature rose to 70°, which temperature was matintained for 4 hours. After cooling, a liquid having two phases was recovered. The denser phase was agitated with 50 $cm^3$ of a 10 percent aqueous solution of NaOH, washed with 100 $cm^3$ of water, dried over anhydrous sodium sulfate and distilled. Two fractions and a residue were obtained;

a. 58°-76° C/200 mm Hg. fraction: This fraction was washed with 50 $cm^3$ of water yielding two phases. The denser phase weighed 47.6 g; it was made up of $C_8F_{17}$—CH=$CH_2$ (88 percent), $C_8F_{17}$—$C_2H_4$—I (4 percent), $C_8F_{17}$—$C_2H_4$—NH—$CH_3$ (1 percent ) and $C_7F_{15}$ —CF=CH—$CH_2$ —NH—$CH_3$ (6 percent).

b. 93°/20 mm Hg. fraction: 93 g containing $C_8F_{17}$—$C_2H_4$—NH—$CH_3$ (16 percent) and $C_7F_{15}$—CF=$CH_2$—NH—$CH_3$.

c. Solid Residue: 2 g, unidentified.

Yield for the experiment were 9 percent for $C_8F_{17}$—$C_2H_4$—NH—$CH_3$ and 52 percent for $C_7F_{15}$—CF=CH—$CH_2$—NH—$CH_3$.

EXAMPLE 22

A mixture of $C_{10}F_{21}$—$C_2H_4$—I (67.4 g) and methyl amine (12.4 g) was dissolved in 100 cm³ pyridine in an 800 cm³ autoclave. The autoclave was cooled with liquid nitrogen and placed under vacuum to remove inert gases. The autoclave was permitted to warm up to ambient temperature, agitation was started and within 30 minutes, the temperature rose to 70°, which temperature was maintained for 3 ½ hrs. After cooling, a liquid having two phases was recovered; a light phase (A) and a dense phase (B). Phase (A) was agitated with 50 cm³ of a 10 percent aqueous solution of NaOH which after decantation yielded a phase (C) which was added to phase (B). Phases (B) and (C) were subjected to four successive extractions with 100 cm³ of ethyl ether, the ether extracts were dried over anhydrous sodium sulfate and distilled. In addition to ethyl ether, four fractions were obtained:

a. 48–58/100 mm Hg. fraction: This fraction contained two phases, the upper phase containing pyridine and the denser phase weighing 2.7 g pyridine (3.5 percent), $C_{10}F_{21}$—CH=$CH_2$ (70.9 percent), $C_{10}F_{21}$—$C_2H_4$—NH—$CH_3$(3.6 percent) and $C_9F_{19}$—CF=CH—$CH_2$—NH—$CH_3$ (20 percent).

b. 58°/100 mm Hg. fraction: containing pyridine.

c. 30°–116°/20 mm Hg. fraction: 2.6 g containing $C_{10}F_{21}$—CH=$CH_2$(40 percent), $C_{10}F_{21}$—CH=$CH_2$ (40 percent), $C_{10}F_{21}$—$C_2H_4$—NH—$CH_3$ (8.4 percent) and $C_9F_{19}$—CF=CH—$CH_2$—NH—$CH_3$ (51.6 percent).

d. 116°–118°/20 mm Hg. fraction: 42.5 g, containing $C_{10}F_{21}$—$C_2H_4$—NH—$CH_3$ (14 percent) and $C_9F_{19}$—CF=CH—$CH_2$—NH—$CH_3$ (86 percent).

Yields for the experiment were 64.5 percent for $C_9F_{19}$—CF=CH—$CH_2$—NH—$CH_3$ and 10.5 percent for $C_{10}F_{21}$—$C_2H_4$—NH—$CH_3$.

EXAMPLE 23

A mixture of $C_6F_{13}$—$C_2H_4$—I (47.4 g, 0.1 mole) and n-butylamine (2-.2g, 0.4 mole), dissolved in 100 cm³ pyridine, was heated with reflux and under continuous agitation at 100–108° C for 4½ hours. This mixture was then distilled from which there were obtained two fractions and a residue:

a. 50° C/100 mm Hg. fraction: This fraction was washed with water, which yielded an aqueous phase at the top and a more dense organic phase. The organic phase, after drying over anhydrous sodium sulfate, weighed 3.1 g; it was made up of 43 percent $C_6F_{13}$—CH=$CH_2$, 27 percent of $C_6F_{13}$—$C_2H_4$—NH—$C_4H_9$ and 30 percent of $C_5F_{11}$—CF=CH—$CH_2$—NH—$C_4H_9$.

b. 52° C/100 mm Hg. fraction: This fraction was essentially made up of pyridine.

c. Residue: The residue was agitated with 30 cm³ of a 10 weight-percent solution of NaOH. The resulting solution was then subjected to five successive extractions with 60 cm³ of ethyl ether, the ether extracts then being dried over anhydrous sodium sulfate. After evaporation of the ether, the liquid was distilled and there were obtained two fractions and a residue:

1. The first fraction weighed 15.6 g and contained n-butylamine and pyridine.

2. 93° C/17 mm Hg. fraction, 29.1 g containing $C_6F_{13}C_2H_4$—NH—$C_4H_9$ (47 percent), and $C_5F_{11}$—CF=CH—$CH_2$—NH—$C_4H_9$ (53 percent).

3. Solid Residue, 2g, made up of the iodohydrate of $C_6F_{13}$—$C_2H_4$—NH—$C_4H_9$ and $C_5F_{11}$—CF=CH—$CH_2$—NH—$C_4H_9$.

The yield of the experiment were 37 percent for $C_6F_{13}$—$C_2H_4$—NH—$C_4H_9$, 42.5 percent for $C_5F_{11}$—CF=CH—$CH_2$—NH—$C_4H_9$ and 4 percent for $C_6F_{13}$—CH=$CH_2$.

EXAMPLE 24

A mixture of $C_8F_{17}$—$C_2H_4$—I (144.5 g) and n-butylamine (73 g) were dissolved in 250 cm³ of pyridine and heated to 100° C under constant agitation for four hours. The reaction medium contained two phases: A volatile phase (A) and dense phase (B). 150 cm³ of water were added to (A) yielding a phase (C) which was added to (B). Then (B) and (C) were mixed with 250 cm³ of a 10 percent aqueous NaOH solution, washed with water and the organic layer was then dried over anhydrous sodium sulfate. Upon distillation, three fractions and a residue were obtained:

a. 30°/10 mm Hg. fraction: This fraction was washed with water and upon decantation yielded $C_8F_{17}$—CH=$CH^2$ (11.2 g).

b. 45°/10 mm Hg. fraction: This fraction yielded 8.3 g of $C_8F_{17}$—$C_2H_4$—NH—$nC_4H_9$ (97 percent).

c. 90°/2–3 mm Hg.: 92.2 g, containing $C_8F_{17}$—$C_2H_4$—NH—$nC_4H_9$ (45 percent) and $C_7H_7F_{15}$—CF=CH—$CH_2$—NH—$nC_4H_9$(55 percent).

d. Residue: weighed 2.2 g.

Yields for the experiment were 32.4 percent for $C_8F_{17}$—$C_2H_4$—NH—$nC_4H_9$ and 39.6 percent for $C_7H_{15}$—CF=CH—$CH_2$—NH—$nC_4H_9$.

EXAMPLE 25

A mixture of $C_4F_9$—$C_2H_4$—I (74.8 g) and diethyl amine (58 g) dissolved in 200 cm³ of pyridine was heated with reflux and under constant agitation at 71°–81° C for 4 hours. Following mixing with 60 cm³ of a 15 percent aqueous solution of NaOH, two phases were obtained. The lighter aqueous phase was subjected to five successive extractions with 50 cm³ of ethyl ether and these ether extracts were then added to the denser organic phase. The ether was evaporated and the liquid distilled. Three fractions were obtained:

a. 45°–75°/250 mm Hg. fraction: After washing, two phases were obtained. The heavier phase after being dried over anhydrous sodium sulfate, weighed 10.3 g. and was made up of $C_4F_9$—$C_2H_4$—$N(C_2H_5)_2$ (7 percent), $C_3F_7$—CF=CH—$CH_2$—$N(C_2H_5)_2$ (31 percent), $C_4F_9$—CH=$CH_2$ (6 percent) and pyridine (6 percent).

b. 50° C/70 mm Hg. fraction: This fraction was treated the same as the preceding fraction and yielded 11.9 g. of $C_4F_9$—$C_2H_4$—$N(C_2H_5)_2$ (6.7 percent), $C_3F_7$—CF=CH—$CH_2$—$N(C_2H_5)_2$ (71 percent), $C_4F_9$—CH=$CH_2$ (18 percent) and pyridine (4 percent)

c. 60° C/15 mm Hg. fraction: 27.2 g, containing $C_4F_9$—$C_2H_4$—$N(C_2H_5)_2$ (95 percent), pyridine (3 percent) and an unidentified substance (2 percent).

Yields for the experiment were 5.6 percent for $C_4F_9$—$C_2H_4$—$N(C_2H_5)_2$, 5.7 percent for $C_4F_9$-CH=$CH_2$ and 64.4 percent for $C_3F_7$—CF=CH—$CH_2$—$N(C_2H_5)_2$.

EXAMPLE 26

A mixture of $C_8F_{17}$—$C_2H_4$—I (75.4 g) and diethyl amine (29.2 g) dissolved in 100 cm³ pyridine was heated at 80° C for 4 hours. A volatile phase (A) and a denser phase (B) were obtained. (A) was mixed with 50 cm³ of a 10 percent aqueous solution of NaOH yielding phase (C) which was then added to (B). (B) and (C) together were agitated with 50 cm³ of a 5 percent aqueous solution of NaOH, and subjected to four successive extractions with 50 cm³ of diethyl ether. The ether extracts were dried over anhydrous sodium sulfate and upon distillation, yielded two fractions:

(a) 43°–84° C/10 mm Hg. fraction: 21.5 g, containing $C_8F_{17}$—CH=$CH_2$ (92 percent), $C_8F_{17}$—$C_2H_4$—I (1 percent) and $C_7F_{15}$—CF=CH—$CH_2$—$N(C_2H_5)_2$ (7 percent).

b. 84° C/5 mm Hg. fraction: 2.2 g, containing $C_8F_{17}$—$C_2H_4$—N—$(C_2H_5)_2$ (6 percent) and $C_7F_{15}$—CF=CH—$CH_2$—$N(C_2H_5)_2$ (94 percent).

Yields were 3 percent for $C_8F_{17}$—$C_2H_4$—$N(C_2H_5)_2$, 44 percent for $C_8F_{17}$—CH=$CH_2$ and 49 percent for $C_7F_{15}$—CF=CH—$CH_2$—$N(C_2H_5)_2$.

EXAMPLE 27

A mixture of $C_4F_9$—$C_2H_4$—I (37.4 g) and cyclohexyl amine (39.4 g) dissolved in 100 cm³ pyridine was maintained between 85/120° C for 5 hours. The mixture was agitated with 80 cm³ of 10 percent aqueous solution of NaOH and upon decantation, yielded a denser organic phase and a lighter aqueous phase. The aqueous phase was extracted five times with 50 cm³ of diethyl ether and the ether extracts were dried over anhydrous sodium sulfate before being added to the organic phase. The ether was evaporated and upon distillation, the liquid yielded four fractions and a residue:

a. 80° C/400 mm Hg. fraction: 56.5 g, containing $C_4F_9$—CH=$CH_2$ (4 percent), $C_5H_5N$ (70.8 percent), $C_6H_{11}$—$NH_2$ (23.4 percent) and $C_4F_9$—$C_2H_9$—NH—$C_6H_5$ (1.2 percent).

b. 100° C/400 mm Hg. fraction: 20 g, containing $C_5H_5N$ (20.4 percent), $C_6H_{11}$—$NH_2$ (77 percent) and $C_4F_9$—$C_2H_4$—NH—$C_6H_{11}$ (2.6 percent).

c. 45°–100° C/20 mm Hg. fraction: 7.3 g, containing $C_5H_5N$ (11 percent), $C_6H_{11}$—$NH_2$ (50.6 percent), $C_4F_9$—$C_2H_4$—NH—$C_6H_{11}$ (14.2 percent) and $C_3F_7$—CF=CH—$CH_2$—NH—$C_6H_{11}$ (24.2 percent).

d. 100°–105° C/20 mm Hg. fraction: 13 g, containing $C_5H_5N$ (3.7 percent), $C_6H_{11}$—$NH_2$ (5.3 percent) and $C_4F_7$—$C_2H_4$—NH—$C_6H_{11}$ (34 percent) and $C_3F_7$—CF=CH—$CH_2$—NH—$C_6H_{11}$ (57 percent)

Yields were 24 percent for $C_4F_9$—$C_2H_4$—NH—$C_6H_{11}$ and 57 percent $C_3F_7$—CF=CH—$CH_2$—NH—$C_6H_{11}$.

EXAMPLE 28

A mixture of $C_6F_{13}$—$C_2H_4$—I (94.8 g) and cyclohexyl amine (79.2 g) dissolved in 200 cm³ of pyridine was heated for 4 hours at 80° C under constant stirring. After completion of the reaction, a volatile phase (A) and a denser phase (B) were separated by decantation. (A) was mixed with 50 cm³ of a 10 percent aqueous solution of NaOH providing phase (C) which was added to (B). Together, (B) and (C) were mixed with a 5 percent aqueous solution of NaOH, washed with 50 cm³ of water and extracted four times with 50 cm³ diethyl ether. The ether extracts were dried over anhydrous sodium sulfate and distilled. Two fractions were obtained:

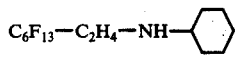

a. 55° C/100 mm Hg. fraction: 39.5, containing $C_6F_{13}$—$C_2H_4$—I (98.5 percent) and

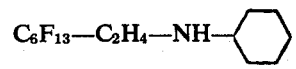

(1.4 percent).

b. 128° C/20 mm Hg. fraction: 26.5 g, containing

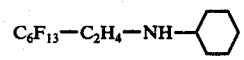

(33 percent) and

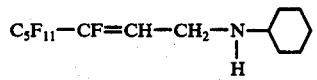

Yields for the experiment were 10 percent for

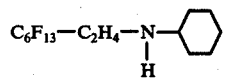

and 21 percent for

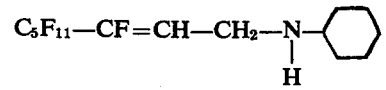

EXAMPLE 29

A mixture of $C_4F_9$—$C_2H_4$—I (33.4 g) and allyl amine (20.3 g) dissolved in 90 cm of pyridine was heated with reflux under constant agitation at 78°–86° C for 4 hours. Upon distillation, a mixture containing three fractions and a residue was obtained:

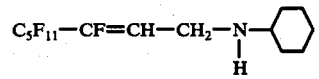

a. 44°–48° C/760 mm Hg. fraction: 6.8 g containing $C_4F_9$—CH=$CH_2$ (63 percent) $C_3F_7$—CF=CH—$CH_2$—NH—$CH_2$—CH=$Ch_2$ (37 percent).

b. 48°–58° C/760 mm Hg. fraction: 6.7 g, containing $C_4F_9$—$CH_2$=CH—$CH_2NH$ $CH_2Cu$=$Cu_2$ (24 percent). Is.$CuF_9CH_2$=CH $CH_2NH_2$(75%)

c. 55° C/100 mm Hg. fraction: containing pyridine. The residue was mixed with 60 cm³, was subjected to five successive extractions with ethyl ether and the ether extracts were dried over anhydrous sodium sulfate. After evaporation of the ether, the liquid yielded, upon distillation, two fractions and a residue:

1. 45°—85° C/50 mm Hg. fraction weighing 2.3 g, containing $C_3F_7$—CF=CH—$CH_2$—NH—$CH_2$—CH=$CH_2$ (63 percent) and an unidentified component (37 percent).

2. 85° C/50 mm Hg. fraction weighing 7.2 g, containing $C_3F_7$—CF=CH—$CH_2$—NH—$Ch_2$—CH=$CH_2$ (98-99 percent).

3. Residue weighing 1 g, consisted essentially of the iodohydrate of $C_4F_9$—$C_2H_4$—NH—$CH_2$—CH=$CH_2$.

Yields were 60 percent for $C_3F_7$—CF=CH—CH$_2$—NH—$CH_2$—CH=$CH_2$ and 19 percent for $C_4F_9$—CH=$CH_2$.

EXAMPLE 30

A mixture of $C_6F_{13}$—$C_2H_4$—I (47.6 g) and allyl amine (22.8 g) dissolved in 100 cm³ of pyridine was heated with reflux under constant agitation at 91°-98° C for 4 hours and upon distillation the liquid yielded three fractions and a residue:

a. 38° C/400 mm Hg. fraction: 12.8 g, upon washing yielded an upper aqueous phase and a lower organic phase, the latter, after having been dried over anhydrous sodium sulfate yielded 3 g of $C_6F_{13}$—CH=$CH_2$.

b. 38°-90° C/400 mm Hg. fraction: The lighter aqueous phase consisted essentially of pyridine and the denser organic phase weighing 6.7 g. containing $C_6F_{13}$—CH=$CH_2$ (94.4 percent).

c. 55° C/100 mm Hg. fraction: containing pyridine.

d. Residue: The residue was mixed with 60 cm³ of a 15 percent aqueous solution of NaOH and the resulting solution was subjected to five successive extractions with diethyl ether, the ether extracts being dried over anhydrous sodium sulfate. After evaporation of the ether, the liquid upon distillation yielded two fractions and a residue:

1 38° C/60 mm Hg. fraction containing 98 percent pyridine.

2. 70° C/5 mm Hg. fraction weighing 21.4 g, containing $C_5F_{11}$—CF=CH—$CH_2$—NH—$CH_2$—CH=$CH_2$ (98 percent).

3. Residue of 1.0 percent was essentially the iodohydrate of $C_5F_{11}$—CF=CH—$CH_2$—NH—$CH_2$—CH=$CH_2$.

Yields for the experiment were 56 percent for $C_5F_{11}$—CF=CH—$CH_2$—NH—$CH_2$—CH=$CH_2$ and 32 percent for $C_6F_{13}$—CH=$CH_2$.

EXAMPLE 31

Into a stainless steel autoclave were introduced 800 cc of $C_2F_5C_2H_4$—I (54.8 g; 0.2 mole), methylamine (24.8 g; 0.8 mole), pyridine (200 cc). The autoclave was cooled in a liquid nitrogen bath, and the inert gasses eliminated by suction under vacuum. The autoclave was allowed to warm up to room temperature, the stirring device started, and the autoclave brought to a temperature of 80° C within 30 minutes. This temperature was maintained during 3 hours 30 minutes. After cooling, a liquid was recovered and stirred with 100 cc of a 10 percent-by-weight aqueous solution of NaOH. The resulting solution was extracted with ethyl ether (6 times 100 cc). After drying the etheral extracts over anhydrous sodium sulfate, they were distilled, and three fractions, in addition to the ethyl ether, were obtained:

a. Fraction 75°-79°: 2.8 g was made up ether (25 percent), of two nonidentified compounds (18 percent), and of $C_2F_5$—$C_2H_4$—NH—$CH_3$ (57 percent);

b. Fraction 80°-82°: 24.8 g was made up of $C_2F_5$—$C_2H_4$—NH—$Ch_3$ (0.12 mole);

c. Fraction 83°-96°: 14 g. This fraction was washed with 10 cc of water, and this brought about the decantation of a dense phase, which, after drying over anhydrous sodium sulfate, weighed (5.1 g). This dense phase is made up of the amine $C_2F_5$—$C_2H_4$—NH—$CH_3$ (0.0247 mole).

The rate of conversion is greater than 73 percent.

EXAMPLE 32

$C_6F_{13}$(—$C_2H_4$)$_2$I (50.2 g; 0.1 mole), ammonia (17 g; 1 mole), ethanol (100 cc) were introduced into an autoclave. The autoclave was cooled in a liquid nitrogen bath, and the inert gases eliminated by suction under vacuum. The autoclave was allowed to warm up to room temperature, then the stirring device was started, and the autoclave brought to a temperature of 90° within 30 minutes. It was kept at this temperature during 3 hours 30 minutes. After cooling, a liquid was recovered, and this was stirred with 50 cc of an aqueous 10 percent solution of NaOH. The resulting solution was then extracted with ethyl ether (6 times 50 cc). The extracts were dried over anhydrous sodium sulfate and, after elimination of the ether by evaporation, the residual liquid was distilled. Three fractions were thus recovered:

a. Fraction 52°/200 mm: 22 g made up of ethanol (99.3 percent) and of $C_6F_{13}$—$C_2H_4$—Ch=$CH_2$ (0.7 percent; 0.0032 mole);

b. Fraction 102°-104°/50 mm: 24.2 made up of $C_6F_{13}(C_2H_4)_2NH_2$ (98 percent; 0.0608 mole) and of an unidentified impurity (2 percent);

c. Fraction 172°-175°/10 mm: 3.1 g made up of $[C_6F_{13}(C_2H_4)_2]_2NH$ (97 percent; 0.0039 mole), and of a non-identified impurity.

The rate of conversion of $C_6F_{13}(C_2H_4)_2NH_2$ is 64 percent.

EXAMPLE 33

$C_8F_{17}(C_2H_4)_2I$ (30.1 G; 0.05 mole), ammonia (13 g; 0.75 mole), ethanol (50 cc) were introduced into an autoclave. The autoclave was cooled in a liquid nitrogen bath and the inert gases were eliminated by suction under vaccum. The autoclave was allowed to warm up to room temperature, then the stirring device was started, and the autoclave brought to a temperature of 80° within 30 minutes. This temperature was kept during 3 hours 30 minutes. After cooling, a liquid containing a solid in suspension was recovered, and this was stirred with 50 cc of a 10 percent aqueous solution of NaOH. The resulting solution was then extracted with ethyl ether (4 times 50 cc). The etheral extracts were dried over anhydrous sodium sulfate and, after elimination of the ether by evaporation, the residual liquid was distilled. Three fractions and a residue were thus recovered:

a. Fraction <78° was made up of two phases. These two phases were stirred with 5 cc of water, and this lead to a clear decantation. The denser phase (1.1 g) is made up of $C_8F_{17}$—$C_2H_4$—CH=$CH_2$;

b. Fraction 78° was made up of ethanol;

c. Fraction 113°-116°/20 mm Hg.: 17.7 g was made up of $C_8F_{17}(C_2H_4)_2NH_2$ (96 percent; 0.034 mole) and of non-identified impurities (4 percent);

d. Solid Residue: 4.1 g was made up of $[C_8F_{17}(C_2H_4)_2]NH$ (97 percent) contaminated with nonidentified impurities (3 percent).

The rates of conversion of $C_8F_{17}(C_2H_4)_2NH_2NH_2$ and $[C_8F_{17}(C_2H_4)_2]NH$ were 68 percent and 17 percent, respectively.

EXAMPLE 34

Into an autoclave of 800 cc capacity, $C_6F_{13}(C_2H_4)_2I$ (25.1 g; 0.05 mole), methylamine (6.2 g; 0.2 mole), and pyridine (50 cc) were introduced. After suction of the inert gases under vacuum, the autoclave was brought to 80°, kept at that temperature for 4 hours. After cooling, a liquid consisting of two phases was recovered. These phases were separated by decantation. The light phast (A) was stirred with 30 cc of a 10 percent aqueous solution of NaOH, and this brought about a phase (C)

which was decanted and added to the dense phase (B). Phases (B) + (C) together were washed with 50 cc of water, then the organic phase was dried over anhydrous sodium sulfate and distilled. Three fractions and a residue were thus recovered:

a. Fraction 50°/100 mm Hg: 5.1 g was made up of pyridine:

b. Fraction 40°–95°/20 mm Hg: 1.9 g was made up of pyridine (12 percent) and of $C_6F_{13}(C_2H_4)_2NH\text{-}Ch_3$ (88 percent; 0.0045 mole);

c. Fraction 96°/20 mm Hg: 14.2 g was made up of $C_6F_{13}(C_2H_4)NH\text{—}CH_2$ (0.035 mole);

d. Solid residue 1 g. Solid not identified.

Conversion rate is 79 percent

We claim:

1. A perfluoroalkyl substituted amine of the formula

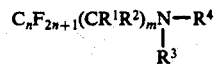

wherein $n$ is an integer from 1 to about 20, $m$ is 2 or 4, $R^1$ and $R^2$ each is hydrogen or alkyl containing 1 to 3 carbon atoms and $R^3$ is hydrogen and $R^4$ is hydrogen or alkenyl containing 3 to 10 carbon atoms.

2. An amine according to claim 1 wherein $n$ is from 6 to 12 and $m$ is 2.

3. An amine according to claim 1 wherein the amine has the formula

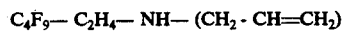

4. An amine according to claim 2 wherein the amine has the formula

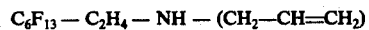

* * * * *

UNITED STATES PATENT AND TRADEMARK OFFICE
CERTIFICATE OF CORRECTION

PATENT NO. : 4,059,629

DATED : November 22, 1977

INVENTOR(S) : Louis Foulletier and Jean-Pierre Lalu

It is certified that error appears in the above-identified patent and that said Letters Patent are hereby corrected as shown below:

Column 6, line 40, reads "other", should read --ether--

Column 12, line 37, reads " .Fraction ", should read -- (b) Fraction --

Column 15, lines 35 and 36, delete formula, second occurrence only, which reads "$C_{10}F_{21}-CH=CH_2$ (40 percent)"

Column 18, line 1, delete formula "$C_6F_{13}-C_2H_4-NH-$ "

Column 18, line 20, insert after formula --(67 percent)--

Column 18, line 37, reads "90 cm", should read --90 $cm^3$--

Column 18, line 43, delete formula " "

UNITED STATES PATENT AND TRADEMARK OFFICE
CERTIFICATE OF CORRECTION

PATENT NO. : 4,059,629

DATED : November 22, 1977

INVENTOR(S) : Louis Foulletier and Jean-Pierre Lalu

Page 2 of 2

It is certified that error appears in the above-identified patent and that said Letters Patent are hereby corrected as shown below:

Column 20, line 17, reads "24.2", should read --24.2 g--

Column 20, line 66, reads "phast", should read --phase--

Signed and Sealed this

Second Day of May 1978

[SEAL]

Attest:

RUTH C. MASON
Attesting Officer

LUTRELLE F. PARKER
Acting Commissioner of Patents and Trademarks